(12) United States Patent
Potma et al.

(10) Patent No.: US 7,388,668 B2
(45) Date of Patent: Jun. 17, 2008

(54) PHASE SENSITIVE HETERODYNE COHERENT ANTI-STOKES RAMAN SCATTERING MICRO-SPECTROSCOPY AND MICROSCOPY

(75) Inventors: Eric O. Potma, Cambridge, MA (US); Conor Evans, Cambridge, MA (US); Xiaoliang Sunney Xie, Lexington, MA (US)

(73) Assignee: President & Fellows of Harvard College, Cambridge, MA (US)

( * ) Notice: Subject to any disclaimer, the term of this patent is extended or adjusted under 35 U.S.C. 154(b) by 177 days.

(21) Appl. No.: 11/145,420

(22) Filed: Jun. 3, 2005

(65) Prior Publication Data
US 2005/0280827 A1 Dec. 22, 2005

Related U.S. Application Data

(60) Provisional application No. 60/578,146, filed on Jun. 9, 2004.

(51) Int. Cl.
G01B 9/02 (2006.01)
(52) U.S. Cl. ...................... 356/451; 356/301
(58) Field of Classification Search ............... 356/301, 356/451
See application file for complete search history.

(56) References Cited

U.S. PATENT DOCUMENTS

| 4,193,690 A | 3/1980 | Levenson et al. |
| 6,108,081 A | 8/2000 | Holtom et al. |
| 2003/0011765 A1 | 1/2003 | Xie et al. |
| 2003/0160955 A1 | 8/2003 | Xie et al. |
| 2005/0168735 A1* | 8/2005 | Boppart et al. ............. 356/301 |

OTHER PUBLICATIONS

Hahn et al, Measurement of nonresonant third-order susceptibilities of various gases by the nonlinear interferometric technique, JOSA B, vol. 12, No. 6, Jun. 1995, pp. 1021-1027.*
Vinegoni et al "Nonlinear optical contrast enhancement for optical coherence tomography", Optics Express, vol. 12, No. 2, Jan. 26, 2004, pp. 331-341.
Marwosky et al. "CARS-Background Suppression by Phase-Controlled Nonlinear Interferometry", Applied Physics B., vol. B51, No. 1, Jul. 1, 1990, pp. 49-51.
Volkmer et al."Vibrational Imaging with High Sensitivity via Epidetected Coherent Anti-Stokes Raman Scattering Microscopy", Physical Review Letters, vol. 87, No. 2, Jul. 9, 2001, pp. 023901-1-023901-4.
Volkmer et al. "Time-resolved coherent anti-Stokes Raman scattering microscopy: Imaging based on Raman free induction decay", applied Physics Letters, vol. 80, No. 9, Mar. 4, 2002, pp. 1505-1507.

* cited by examiner

*Primary Examiner*—Samuel A Turner
(74) *Attorney, Agent, or Firm*—Gauthier & Connors LLP (57) ABSTRACT

A system is disclosed for detecting a non-linear coherent field induced in a sample volume. The system includes a first source for generating a first electromagnetic field at a first frequency, a second source for generating a second electromagnetic field at a second frequency, first optics for directing the first and second electromagnetic fields toward the sample volume, second optics for directing the first and second electromagnetic fields toward a local oscillator volume, and an interferometer. The interferometer is for interfering a first scattering field that is generated by the interaction of the first and second electromagnetic fields in the sample volume, with a second scattering field that is generated by the interaction of the first and second electromagnetic fields in the local oscillator volume.

20 Claims, 7 Drawing Sheets

PHASE SENSITIVE HETERODYNE COHERENT ANTI-STOKES RAMAN SCATTERING MICRO-SPECTROSCOPY AND MICROSCOPY

This application claims priority to U.S. Provisional Patent Application Ser. No. 60/578,146 filed Jun. 9, 2004.

This invention was sponsored, at least in part, by Grant No. GM062536 from the National Institute of Health (NIH) and the United States government has certain rights to the invention.

BACKGROUND

The present invention generally relates to microscopy systems, and relates in particular to coherent anti-Stokes Raman scattering (CARS) vibrational imaging.

CARS vibrational imaging has been shown to be a powerful tool in biology due to its ability to visualize biological samples with high sensitivity without the necessity of labeling with fluorophores. Despite its sensitivity, CARS microscopy is hampered, however, by the presence of a non-resonant background signal that is intrinsically generated along with the vibrational specific signal. CARS arises from the third order nonlinear susceptibility $\chi^{(3)}$, which is a sum of a vibrationally resonant part $\chi_{res}^{(3)}$, and a non-resonant electronic contribution $\chi_{nr}^{(3)}$. The background overwhelms weak resonant signals and contaminates the signal through coherent mixing, preventing straightforward reconstruction of the resonant signal of interest. The existence of a non-resonant background is a primary limitation that limits further sensitivity improvement of CARS microscopy. For certain biological and clinical applications of CARS microscopy, complete suppression of the background and full extraction of the resonant signal are desirable.

In addition to the non-resonant background, there are several other limitations constraining the current state-of-the-art CARS microscopes. First, the CARS signal scales quadratically with the concentration of the molecular entities under study. This hinders a quantitative assessment of weak signals. A linear dependence of the signal on the concentration would benefit a quantitative analysis of the acquired images and spectra. Second, current state-of-the-art CARS microscopes do not offer the possibility of amplifying weak signals. Weak CARS signals are difficult to detect, and a means of amplifying these weak signals would be highly beneficial. Lastly, the resonant contrast results from the Raman activity of molecules. Even though spontaneous Raman cross-sections and spectra of a vast amount of biochemical compounds are well-documented in literature, the CARS signal cannot be directly compared with the Raman literature values. This difficultly in correlating between CARS signals and spontaneous Raman values further limits the application of CARS microscopy as a routine imaging tool.

Suppression of the non-resonant background in CARS microscopy by detecting the CARS signal in a reverse or backward direction is disclosed in U.S. Pat. No. 6,809,814. Systems disclosed therein, however, do not suppress the contribution from sub-wavelength sized non-resonant features in focus with nonlinear susceptibilities different from that of water. Such systems also do not provide for the amplification of weak signals, or provide a methodology for quantitatively relating the CARS signal to Raman cross-section values.

Suppression of the non-resonant background in CARS microscopy by using differently polarized pump and Stokes fields is disclosed in U.S. Pat. No. 6,798,507. Suppression of the background by use of an analyzer (polarizer) not only results in rejection of the non-resonant contribution of the signal, but also may attenuate the resonant contribution. Application of the polarization sensitive microscope may be, therefore, limited to those studies in which the resonant signal is particularly strong. Also, isolation of $\text{Im}\chi_{res}^{(3)}$ is not possible with the polarization CARS microscope, preventing a direct comparison with Raman cross-sections.

There is a need, therefore, for a system and method for providing improved sensitivity of CARS microscopy, and in particular to provide CARS detection with improved imaging of weak CARS signals. There is also a need to provide for comparison of CARS signals with spontaneous Raman values for a variety of bio-chemical compounds.

SUMMARY

In accordance with an embodiment, the invention provides a system for detecting a non-linear coherent field induced in a sample volume. The system includes a first source for generating a first electromagnetic field at a first frequency, a second source for generating a second electromagnetic field at a second frequency, first optics for directing the first and second electromagnetic fields toward the sample volume, second optics for directing the first and second electromagnetic fields toward a local oscillator volume, and an interferometer. The interferometer is for interfering a first scattering field that is generated by the interaction of the first and second electromagnetic fields in the sample volume, with a second scattering field that is generated by the interaction of the first and second electromagnetic fields in the local oscillator volume.

In accordance with another embodiment, the invention provides a system for facilitating the detection of a non-linear coherent field induced in a sample volume. The system includes a first source input for receiving a first electromagnetic field at a first frequency, a second source input for receiving a second electromagnetic field at a second frequency, output optics for directing the first and second electromagnetic fields toward the sample volume, and local oscillator optics. The local oscillator optics are for directing the first and second electromagnetic fields toward a local oscillator volume, and for providing that a first scattering field that is generated by the interaction of the first and second electromagnetic fields in the local oscillator volume is also directed toward the sample volume such that interference occurs between the first scattering field and a second scattering field that is generated by the interaction of the first and second electromagnetic fields in the sample volume.

In accordance with yet another embodiment, the invention provides a method of detecting a non-linear coherent field induced in a sample volume. The method comprising the steps of generating a first electromagnetic field at a first frequency, generating a second electromagnetic field at a second frequency, directing said first and second electromagnetic fields through a first focusing lens toward the sample volume, directing said first and second electromagnetic fields through a second focusing lens toward a local oscillator volume, and interfering a first scattering field that is generated by the interaction of the first and second electromagnetic fields in the sample volume, with a second scattering field that is generated by the interaction of the first and second electromagnetic fields in the local oscillator volume. The method also includes the step of providing an interference signal responsive to the interference of the first scattering field and the second scattering field.

BRIEF DESCRIPTION OF THE DRAWINGS

The following description may be further understood with reference to the accompanying drawings in which.

The drawings are shown for illustrative purposes only.

DETAILED DESCRIPTION OF THE ILLUSTRATED EMBODIMENTS

In accordance with an embodiment, the invention provides a CARS microscope system that is capable of isolating and amplifying the vibrational resonant signal of interest. In various embodiments, systems of the invention provide CARS detection with improved imaging of weak CARS signals, and provide for suppresion of the nonresonant background signal. In accordance with certain embodiments, a system of the invention generates resonant signals that are linear in the concentration of the molecular entities under study. Moreover, the signal generated may be directly compared with the spontaneous Raman data found in literature.

One solution to the problem of the non-resonant background lies in taking advantage of a fundamental difference between the resonant and non-resonant nonlinear susceptibilities: while $$\chi^{(3)}_{nr}$$

has only a real component, $$\chi^{(3)}_{res}$$

has both real and imaginary parts. The imaginary part of $$\chi^{(3)}_{res}$$

is proportional to the spontaneous Raman cross-section ($S_{Raman} \propto \text{Im}\{\chi^{(3)}\}$). If the imaginary part could be determined, one could obtain the resonant information. As the imaginary part of the field is delayed from the real part by 90 degrees, a direct way of extracting the resonant information is through careful phase control, as can be achieved by heterodyne mixing with a local oscillator field.

Heterodyne detection involves the generation of a separate well-characterized CARS field called the local oscillator, which is linearly mixed with the signal from the sample. The phase of local oscillator relative to the signal field may be controlled, thereby controlling the degree of constructive and destructive interference between the signal and the local oscillator fields. This phase control provides a method of precise amplitude and phase determination of the signal field, which, in turn, provide the real and imaginary contributions to the signal.

Heterodyne detection offers a number of attractive qualities. First, the imaginary part of the signal is uniquely isolated, free from interfering contributions of the non-resonant background. Second, the imaginary component can be directly equated to spontaneous Raman scattering cross-sections and Raman spectral profiles. Third, the heterodyne signal is linearly proportional to concentration, which permits a straightforward quantitative interpretation of images. Fourth, heterodyne mixing provides the possibility of amplifying weak CARS signals by mixing with a strong local oscillator field. Using heterodyne detection schemes with microscopy, therefore, provides selective detection and amplification of resonant signals.

Two configurations are used to heterodyne a local oscillator field to the signal field: parallel and serial interferometry. In parallel interferometry, the local oscillator and signal fields are generated in separate locations and are mixed together to generate interference. In serial interferometry, the local oscillator field is generated first and is sent into the sample along with the pump and Stokes beams. The interference occurs at the point of signal generation when the local oscillator field interferes with the newly created signal field in the focal volume. The serial approach is advantageous over the parallel approach as it can be combined with existing commercial microscopes with little modification.

Figure 1A:
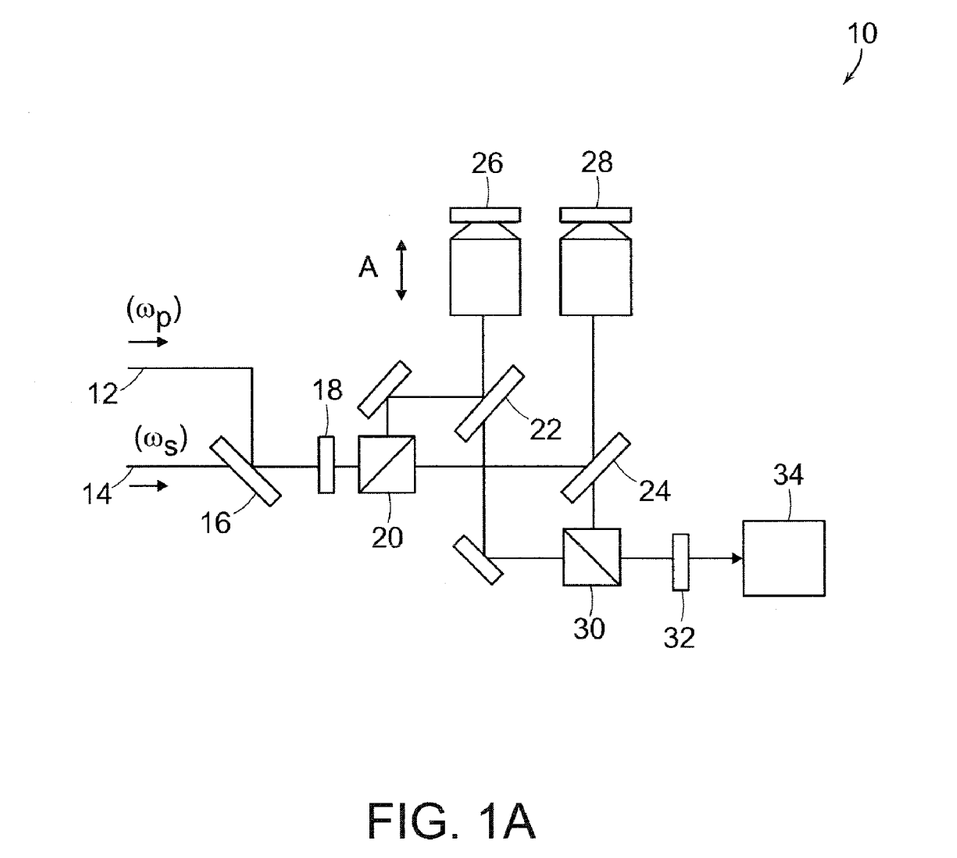
FIGS. 1A and 1B show illustrative diagrammatic views of parallel and serial interferometer systems in accordance with certain embodiments of the invention.

An implementation of heterodyne detection in a parallel interferometric microscope configuration in accordance with an embodiment is shown in FIG. 1A. The system allows for a particular setting of the phase of the local oscillator field that allows selective and direct extraction of the $$\text{Im}\chi^{(3)}_{res}$$

contribution to the CARS signal field. This approach may be applied to CARS microspectroscopy as well as to CARS imaging. The features of the heterodyne CARS microscope, such as the linear dependence of the signal on the concentration and the signal's straightforward connection with spontaneous Raman data, are completely unique to the disclosed technique.

As shown in FIG. 1A a system 10 of an embodiment may be based in part on the principles of a Mach-Zehnder interferometer. The system 10 includes pump and Stokes sources that provide pump and Stokes signals 12 and 14, a dichroic mirror 16, a spectral filter 18, a cubic beamsplitter 20, shortwave pass dichroic mirrors 22, 24, a local oscillator path 26 (including a local oscillator volume and objective lenses), a sample path 28 (including a sample volume and objective lenses), another cubic beamsplitter 30, a 40 nm bandwidth bandpass filter 32 and a detector 34. The microscope objectives may include two identical high numerical aperture lenses.

The two collinearly propagating pulsed excitation (pump and Stokes) beams are split in two parts by the cubic beamsplitter 20. The resulting fractions of the linearly polarized beams are sent into the two paths 26 and 28 of the interferometer. The intensities of the excitation beams are controllable through attenuation filters. Typically the excitation intensity in the local oscillator path 26 exceeds the excitation intensity in the sample arm 28. The path length of the local oscillator path 28 is adjustable with a stepper motor and a piezoelectric scanner for precise phase control as indicated at A. The CARS signals generated in each of the arms are collimated in the backward (epi-) direction (as disclosed, for example, in U.S. Pat. No. 6,809,814, the disclosure of which is hereby incorporated by reference), and separated from the incident radiation by dichroic mirrors 22 and 24. The CARS signals from both arms are combined in the second cubic beamsplitter 30. The combined beams are then detected either by a detector 34 that may be equipped with a spectrometer or may be detected by a spectrally integrated detector.

Figure 1B:
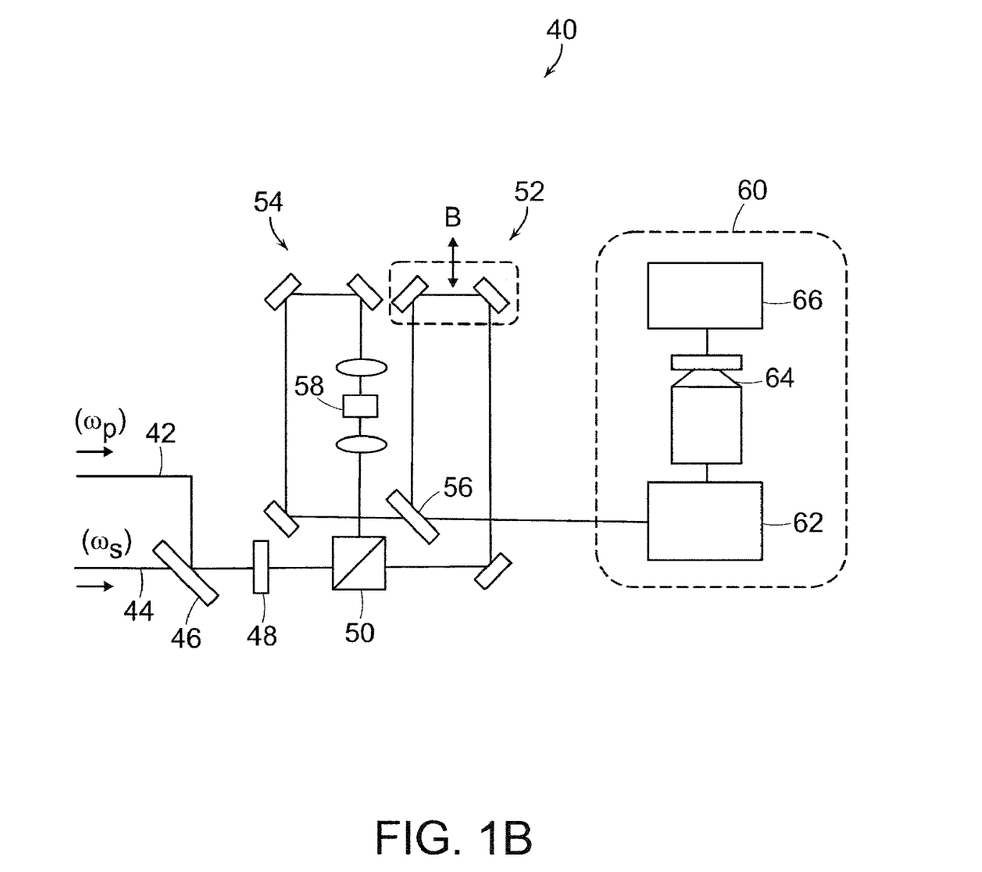

An implementation of heterodyne detection in a serial interferometric microscope configuration in accordance with an embodiment is shown in FIG. 1B. The system also allows for a particular setting of the phase and may be applied to CARS microspectroscopy as well as to CARS imaging. This embodiment retains all the features of the heterodyne CARS microscope embodied in 1A.

As shown in FIG. 1B a system 40 of another embodiment may also be based in part on the principles of a Mach-Zehnder interferometer. The system 40 includes pump and Stokes sources that provide pump and Stokes signals 42 and 44, a dichroic mirror 46, a spectral filter 48, a cubic beamsplitter 50, an adjustable length pump and Stokes path 52 (adjustable as indicated at B), and a local oscillator path 54. The output of the pump and Stokes path 52 is combined with the output of the local oscillator path 54 at another dichroic mirror 56. The local oscillator path 54 includes a local oscillator volume 58 and associated objective lenses. The combined output of the dichroic mirror 56 is provided to a commercial scanning microscope 60 that includes a scanner 62, an objective lens and sample volume unit 64, and a detector 66.

The two collinearly propagating pulsed excitation (pump and Stokes) beams are split in two parts by the cubic beamsplitter 50. The resulting fractions of the linearly polarized beams are sent into the two paths 52 and 54 of the interferometer. The intensities of the excitation beams are controllable through attenuation filters. The path length of the delay path 52 is adjustable with a micrometer and a piezoelectric scanner for precise phase control as indicated at B. The local oscillator CARS signal generated in the local oscillator path is combined with the time delayed pump and Stokes beams on the shortwave pass dichroic mirror 56 and sent into the commercial microscope 60. Operation of the commercial microscope generates a CARS signal field that is interfered with the local oscillator field in the focal volume. The interfered beams are then detected by the microscope's detector that may be an intensity detector or a spectrally integrated detector.

In various embodiments, the invention may provide different versions of a heterodyne CARS microscope, and these versions may differ in their mode of excitation and detection.

For example, a spectrally resolved and spatially stationary CARS interferometer for microscopy may be developed that includes an apparatus for resolving the real and imaginary parts of CARS spectra $$(\chi_{res}^{(3)})$$

recorded from microscopic volumes. In such a system, the beam is focused onto a specific location of the sample at which the spectral real and imaginary components $$\chi_{res}^{(3)}$$

are to be determined. This approach is based on broadband excitation scheme that employs a picosecond pulsed Pump beam and a femtosecond pulsed, broadband Stokes beam. The broadband CARS signals from the sample and the local oscillator, which are generated in the two paths of the interferometer, are interfered with one another and the resulting spectral interferogram is recorded with a spectrometer.

In accordance with another example, a spatially resolved and spectrally stationary CARS interferometer for microscopy may be developed that includes an apparatus for measuring the imaginary part of $$\chi_{res}^{(3)}$$

for a particular point in the spectrum as a function of spatial position. The corresponding spatial map yields a CARS image that is free of background, linear in concentration and proportional to the Raman cross-sections of the entities in focus. This approach employs a narrow-band, picosecond pulsed Pump beam and a narrow-band, picosecond pulsed Stokes beam. The narrowband CARS signal from the sample and local oscillator, which are generated in the two paths of the interferometer, are interfered with one another and detected by a photodetector. For recording the imaginary part only, the phase-difference between the sample path and local oscillator path is set to 90 degrees. To suppress the local oscillator background, a phase-modulator is used in conjunction with a lock-in amplifier.

The method of using CARS interferometer for microspectroscopy is based on spectral interferometry. A broadband CARS field $E_s(\omega)$ from the sample path is interfered with a broadband CARS local oscillator field $E_{lo}(\omega)$ generated from a non-resonant sample in the local oscillator path. The interference appears as a sinusoidal modulation on the detected spectral intensity:

$$S_{CARS}(\omega) = |E_{lo}|^2 + |E_s(\omega)|^2 + 2|E_{lo}E_s(\omega)|\cos\Phi(\omega) \quad (1)$$

where $\Phi(\omega) = \omega\tau + \phi_s(\omega) + \phi_{inst}(\omega)$ is the total phase difference between the fields. In this cases, $\tau$ is the temporal delay between the two arms of the interferometer, $\phi_s(\omega)$ is the phase difference introduced by the sample and $\phi_{inst}(\omega)$ is the relative phase delay due to optical components in the interferometer. The phase information is encoded in the spectral fringe spacing and may be extracted from the spectral interferogram. Once $\phi_s(\omega)$ is known, the real and imaginary components of $\chi^{(3)}(\omega)$ can be readily determined (Re $\chi^{(3)} \propto |E_s(\omega)| \cos \phi_s(\omega)$ and Im $\chi^{(3)}(\omega) \propto |E_s(\omega)| \sin \phi_s(\omega)$, respectively).

Figure 2:
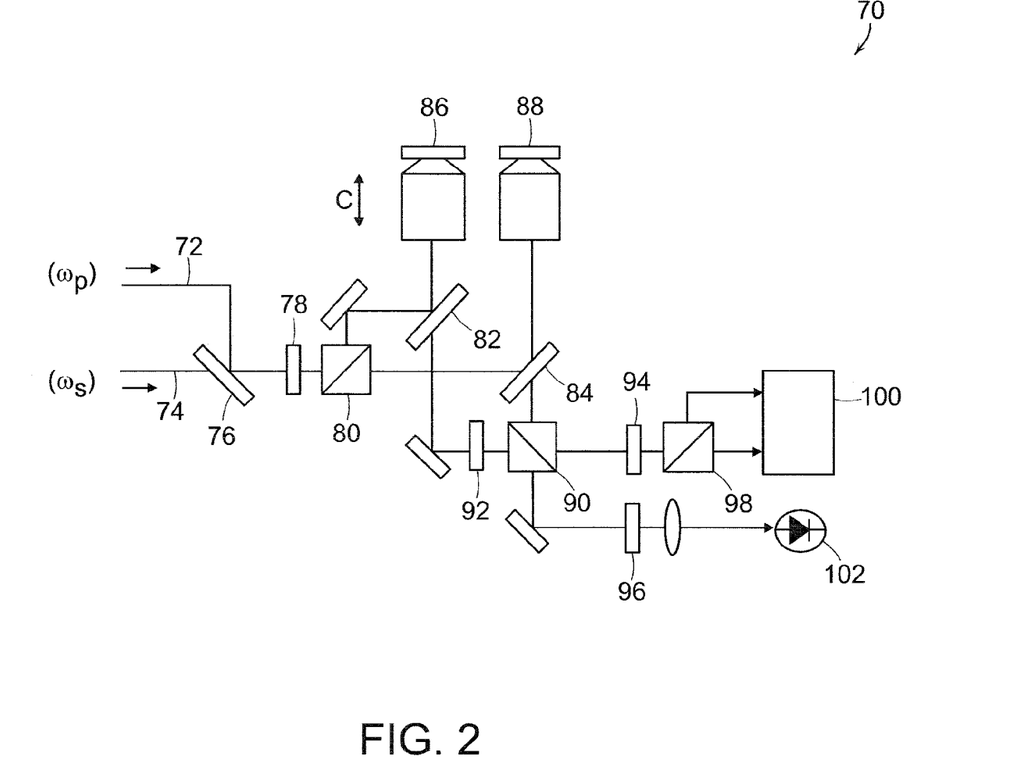
FIG. 2 shows an illustrative diagrammatic view of a spectral interferometer system in accordance with another embodiment to the invention.

An experimental setup for such a system in the parallel epi-configuration is shown in FIG. 2. The system 70 includes pump and Stokes sources that provide pump and Stokes signals 72 and 74, a dichroic mirror 76, a spectral filter 78, a cubic beamsplitter 80, shortwave pass dichroic mirrors 82, 84, a local oscillator path 86, a sample path 88, another cubic beamsplitter 90, a quarter waveplate 92, two 40 nm bandwidth bandpass filters 94 and 96, a polarizing beamsplitter 98, a grating spectrometer charge-coupled device 100 and a single photon avalanche photodiode 102. The microscope objectives may include two identical high numerical aperture lenses.

The microspectroscopy system employs a narrowband, picosecond pump beam and a broadband, femtosecond Stokes beam. To control the relative lengths of the Mach-Zehnder interferometer paths, both a stepper motor and a closed-loop piezo scanner are installed serially on the local oscillator path to allow both coarse and fine path length adjustments as shown at C. In the sample path, the pump and Stokes beams are focused into the sample using a high numerical aperture lens. An identical lens is used in the local oscillator (LO) path to generate the local oscillator field from non-resonant sample such as a glass coverslip/air interface. Both CARS signal and local oscillator fields are collected in the reverse or backward direction (epi-direction) and are separated from the pump and Stokes beams by the dichroic mirrors 82, 84. The two CARS beams are then combined by the cubic beamsplitter 90 that directs the mixed signal simultaneously to spectral and temporal detectors. Spectral interferograms are monitored with a spectrometer equipped with the detector 100 such as a nitrogen-cooled CCD. The single photon avalanche photodiode 102 is used in conjunction with a piezo scanner for recording temporal interferograms.

Spectrally resolved phase information may be extracted from the interferograms using a method developed by Lepetite et al. The CARS beam from the sample is passed through the quarter wave plate 92 and converted to a circular polarized beam. After combination with the local oscillator CARS beam at the beamsplitter 90, the polarizing beam splitter 90 (which is set at 45 degrees to the local oscillator polarization) splits the mixed CARS beam into two orthogonally polarized components. These two linearly polarized beams are then spectrally dispersed and the two separate interferograms are simultaneously detected by the CCD 100. As there is a $\pi/2$ phase shift between the two resulting spectrograms, dividing one by the other yields the tangent of total spectral phase $\Phi(\omega)$.

Figure 3A:
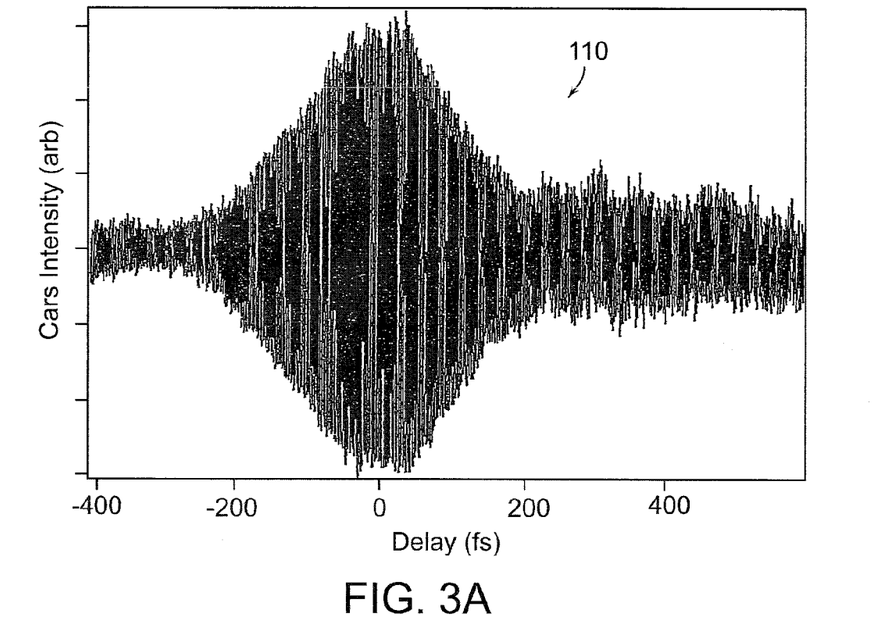
FIGS. 3A and 3B show illustrative diagrammatic graphical representations time domain and spectral domain CARS interferograms of a sample in a system in accordance with an embodiment of the invention.
Figure 3B:
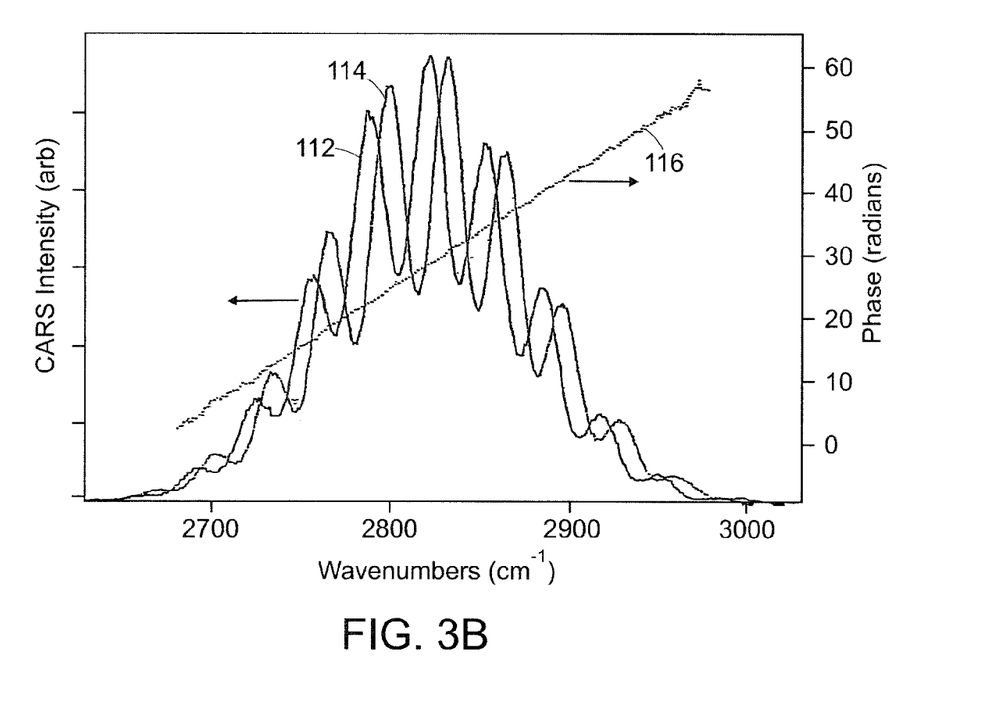

FIGS. 3A and 3B show a comparison of time-domain and spectral domain CARS interferograms. In particular, FIG. 3A shows a temporal interferogram 110 of dodecane recorded with the Raman shift is tuned to the CH-stretching vibrational band around 2845 cm$^{-1}$ (the long tail at positive time delays results from narrow vibrational linewidths). FIG. 3B shows spectral interferograms of two simultaneously collected orthogonally polarizationed signals 112, 114 from a non-resonant sample (glass coverslip) with the paths offset by 1 ps (solid lines). The extracted $\Phi_{ref}(\omega)$ phase is indicated by the dashed line as indicated at 116.

In principle, a temporal interferogram has the same phase information as its spectral counterpart. In practice, however, amplitude and phase determination from a temporal interferogram requires a Fourier transformation of high quality data that must be obtained from temporal scanning. The recording of the spectral interferogram in FIG. 3B required no scanning, was shot noise limited, and was completely insensitive to temporal laser fluctuations.

Figure 4A:
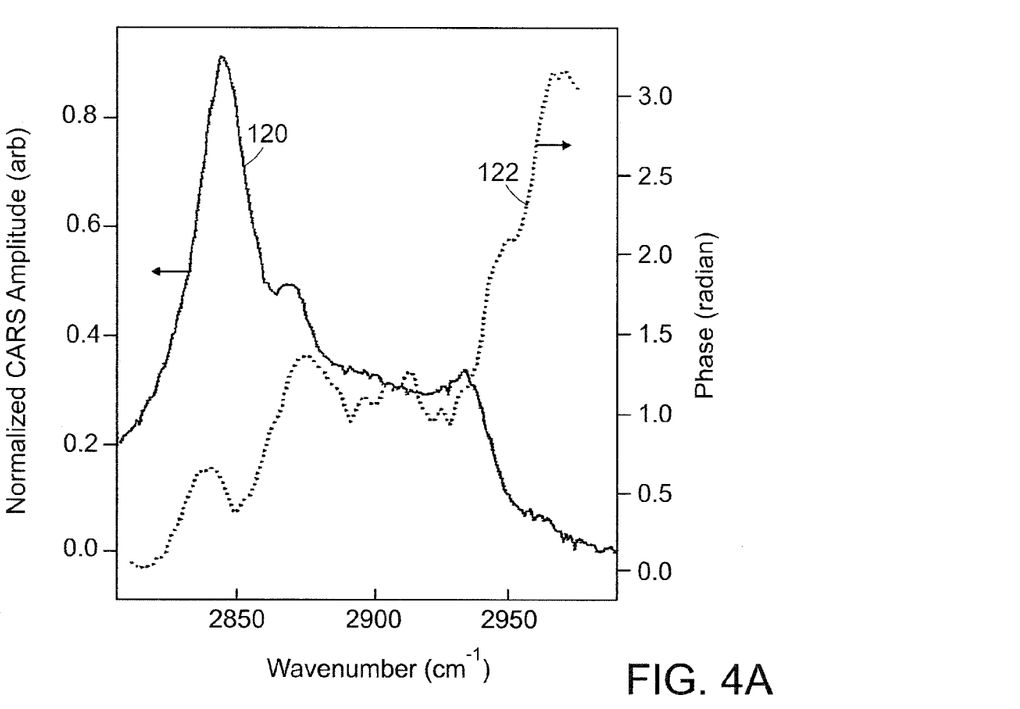
FIGS. 4A and 4B show illustrative diagrammatic graphical representations of CARS spectral amplitude and phase and real and imaginary spectra of a sample in a system in accordance with an embodiment of the invention.
Figure 4B:
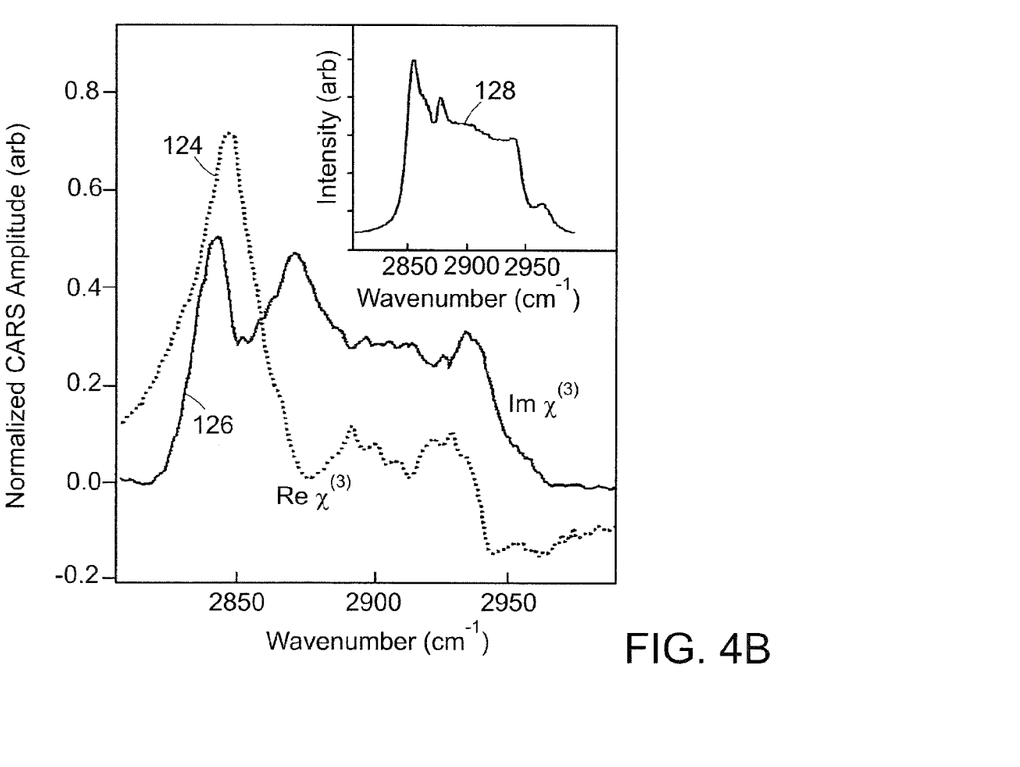

When the non-resonant sample is replaced by a resonant sample, it is straightforward to ascertain the resonant spectral phase profile. FIGS. 4A and 4B show spectral amplitude and phase of the CH-stretching vibrational band of dodecane. FIG. 4A shows extracted CARS amplitude (solid line) at 120 and phase (dotted line) at 122 from the spectral interferograms. FIG. 4B shows the reconstructed Real (dotted line) part of the CARS spectrum at 124 and the Imaginary (solid line) part of the CARS spectrum at 126. The inset shows the Raman spectrum at 128 of dodecane in the CH-stretch vibrational range for comparison, pointing out the similarity between the spontaneous Raman spectrum and the imaginary CARS spectrum. The reconstructed imaginary spectrum is purely resonant and free of non-resonant background contributions, with all the features of the Raman spectrum reproduced.

In accordance with further embodiments, the invention also provides that a CARS interferometer system may be used for microscopy as follows. In CARS interferometric imaging, a narrow-bandwidth CARS field $E_s$ generated in the sample path is interfered with a narrow-bandwidth local oscillator field $E_{lo}$ that is generated in the local oscillator path. The combined fields are detected by an intensity photodetector. The total signal may then be written as:

$$S_{CARS} = |E_{lo}|^2 + |E_s|^2 + 2E_{lo}\{ReE_s\}\cos\Phi + 2E_{lo}ImE_s \sin\Phi \quad (2)$$

where $\Phi$ is the total phase difference between the paths. The last two terms are the heterodyne terms, which depend on the setting of the phase difference. If the phase is set to 90 degrees, the cosine term vanishes while the sine term is maximized. The latter scales linearly with the $E_{lo}$ and, importantly, with the imaginary contribution to the CARS field. This imaginary contribution is again proportional to Im $\chi^{(3)}$, the quantity of interest. To isolate Im $\chi^{(3)}$ from the total signal, the first three terms need to be suppressed. The contributions $|E_{lo}|$ and $|E_s|^2$ may be conveniently eliminated by means of phase modulation and lock-in detection, while the third term may be eliminated by setting the phase to 90 degrees.

Figure 5:
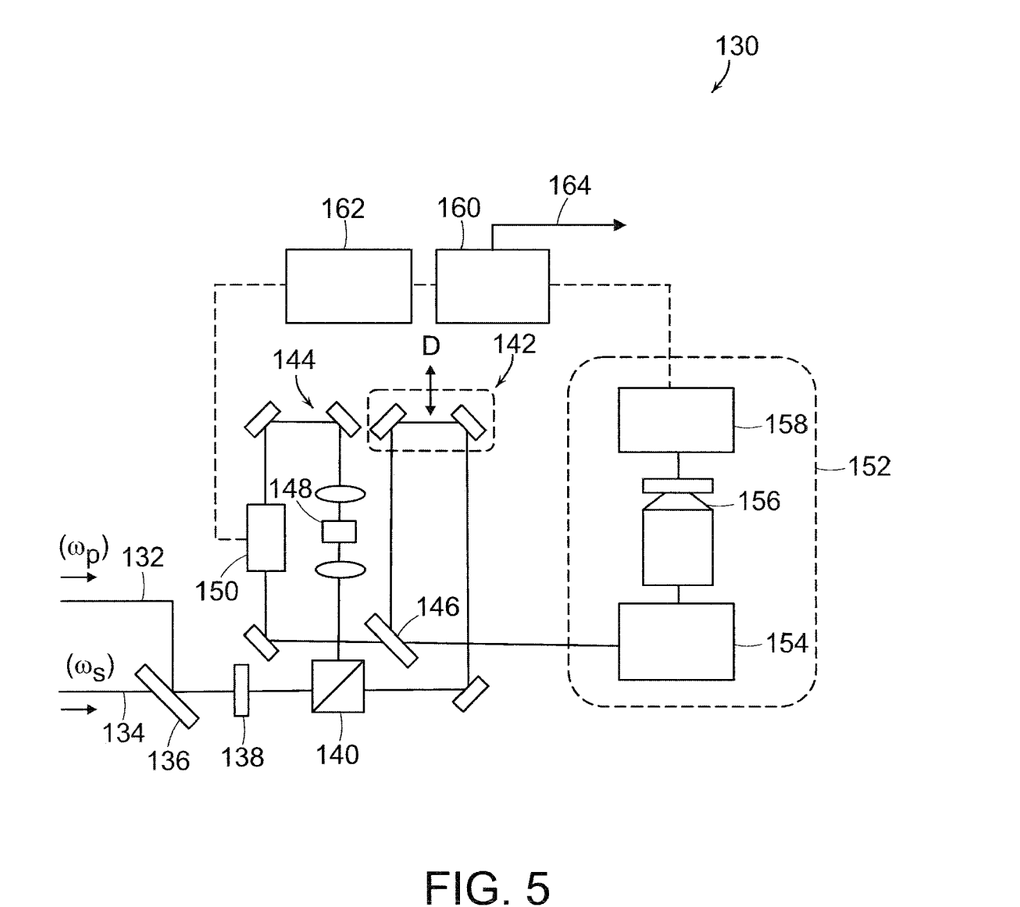
FIG. 5 shows an illustrative diagrammatic view of a serial imaging interferometer system in accordance with an embodiment of the invention.

FIG. 5 shows a system 130 of the CARS imaging interferometer microscope setup based on a serial configuration utilizing forward detection. The system 130 includes pump and Stokes sources that provide pump and Stokes fields 132 and 134, a dichroic mirror 136, a spectral filter 138, a cubic beamsplitter 140, a pump and Stokes path 142 (whose path length may be adjusted as shown at D), a local oscillator path 144, and a shortwave pass dichroic mirror 146. The local oscillator path 144 includes a local oscillator volume 148 and a phase modulator 150. The combined pump, Stokes and local oscillator path output signals are combined and directed toward a commercial beam scanning microscope 152 that includes a scanner 154, a high numerical aperture lens 156, and a photodetector 158 such as a photomultiplier.

In the local oscillator path 144, a local oscillator field is generated. The phase modulator 150 applies a high frequency (10 MHz, for example) phase shift onto the LO field. The LO beam is overlapped with the pump and Stokes beams from the signal path, and directed to a commercial microscope in which raster scanning is performed by rapidly scanning the beams with the beam scanner. The CARS field generated in the sample volume is mixed with the pre-generated local oscillator field. As a consequence, the heterodyne CARS signal is now modulated at the modulation frequency. The heterodyne signal may be isolated by feeding the photomultiplier signal into a lock-in amplifier 160 (such as a phase locked loop). The lock-in amplifier 160 also receives a phase modulation signal from the phase modulator 150 via a driver 162. The filtered signal from the lock-in amplifier 160 is then sent to the computer as shown at 164, which plots the signal as a function of the scanner position.

Figure 6A:
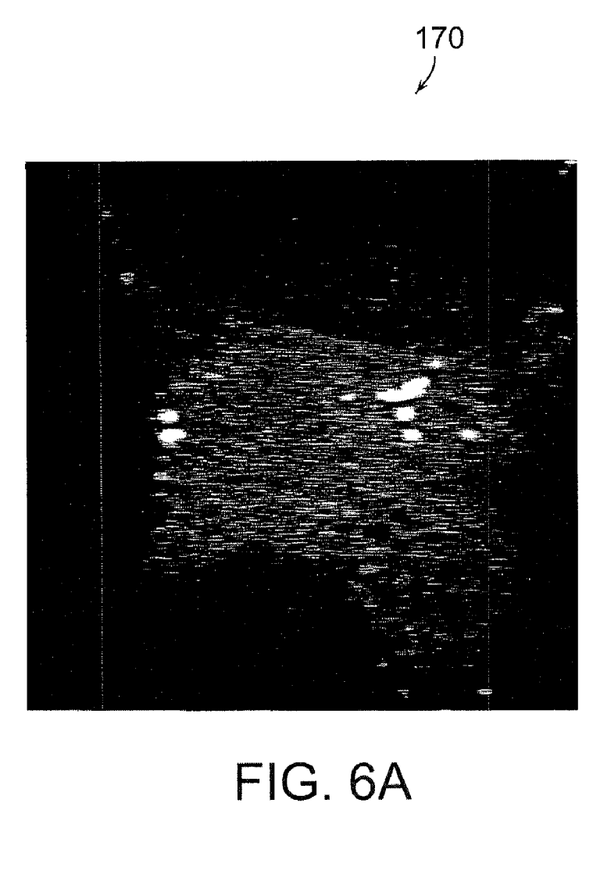
FIGS. 6A and 6B show illustrative recorded CARS images with contrast derived from the imaginary and real responses respectively of a biological sample in accordance with an embodiment of the invention.
Figure 6B:
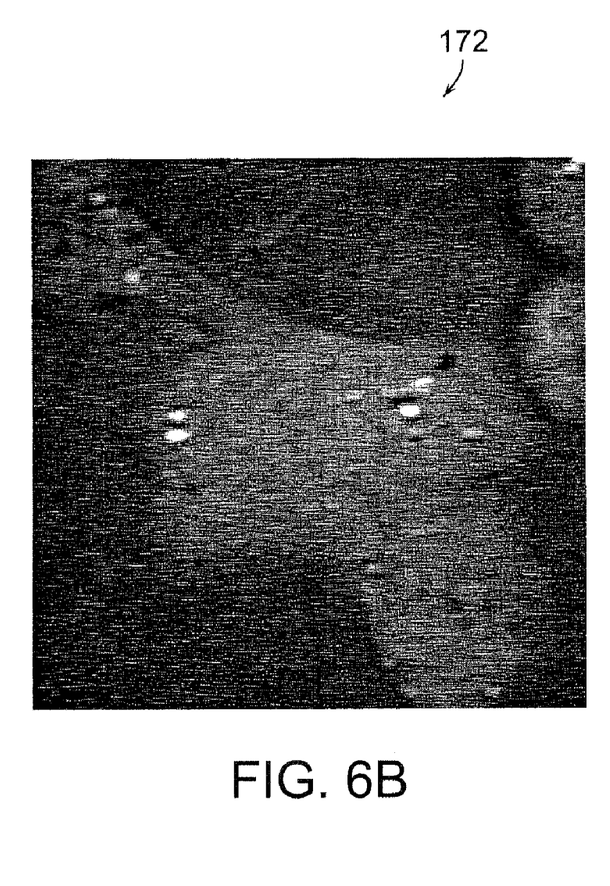

By controlling the phase between the local oscillator field and the CARS field through the piezo-controlled delay stage, both the real and imaginary parts of the signal can be detected separately. In FIG. 6A the imaginary components of the CARS signal from a live mammalian cell is shown at 170, and in FIG. 6B, the real component of the same CARS signal is shown at 172. Setting $\Phi$ to 90 degrees reveals solely the imaginary signal, while the phase setting $\Phi=0$ measures exclusively the real part of the CARS signal. The imaginary image is free of non-resonant background, is linear in the concentration and is linearly amplified with the adjustable amplitude of the local oscillator field. The resulting image is directly related to the corresponding spontaneous Raman image, albeit that image acquisition with CARS is more than four orders of magnitude faster than with spontaneous Raman scattering.

In further embodiments, an epi-detected version of the interferometric CARS microscope may be realized by using an additional cubic beamsplitter in the collimated beam path and by de-scanning the collimated beams prior to epi-detection. In addition, the beam scanner may be replaced by a sample scanner such as a 2D piezo-controlled stage.

Those skilled in the art will appreciate that numerous modifications and variations may be made to the above disclosed embodiments without departing from the spirit and scope of the invention.

What is claimed is:

1. A system for detecting a non-linear coherent field induced in a sample volume, said system comprising:
    a first source for generating a first electromagnetic field at a first frequency;
    a second source for generating a second electromagnetic field at a second frequency;
    first optics for directing a first portion of said first electromagnetic field and a first portion of said second electromagnetic field toward the sample volume;
    second optics for directing a second portion of said first electromagnetic field and a second portion of said second electromagnetic field toward a local oscillator volume;
    third optics for combining a first scattering field that is generated by the interaction of the first portion of the first electromagnetic field and the first portion of the second electromagnetic field in the sample volume, with a second scattering field that is generated by the interaction of the second portion of the first electromagnetic field and the second portion of the second electromagnetic field in the local oscillator volume; and
    a detector system for determining at least one of a real component and an imaginary component of the first scattering field responsive to the first and second scattering fields, wherein said sample volume and said local oscillator volume are positioned in optical paths that are functionally in series with one another.

2. The system as claimed in claim 1, wherein the first scattering field has a first phase and the second scattering field has a second phase that is different than the first phase.

3. The system as claimed in claim 2, wherein at least one of said first phase and said second phase is varied independent of the other of said first phase and said second phase.

4. The system as claimed in claim 1, wherein said system includes computation means for determining amplitude information and phase information of the first scattering field responsive to an output signal provided by an interferometer.

5. The system as claimed in claim 1, wherein a path length difference between a path length of the first scattering field relative to a path length of the second scattering field is changed.

6. The system as claimed in claim 1, wherein said system is used for micro-spectroscopy.

7. The system as claimed in claim 1, wherein said system is used for microscopy.

8. The system as claimed in claim 7, wherein said sample volume and said local oscillator volume are positioned in optical paths that are functionally parallel with one another.

9. The system as claimed in claim 1, wherein said second scattering field is directed through at least a portion of the first optics together with the first and second electromagnetic fields.

10. The system as claimed in claim 1, wherein said system further includes a phase locked amplifier that is coupled to a detector.

11. A method of detecting a non-linear coherent field induced in a sample volume, said method comprising the steps of:
    generating a first electromagnetic field at a first frequency;
    generating a second electromagnetic field at a second frequency;
    directing a first portion of said first electromagnetic field and a first portion of said second electromagnetic field through a first focusing lens toward the sample volume;
    directing a second portion of said first electromagnetic field and a second portion of said second electromagnetic field through a second focusing lens toward a local oscillator volume;
    interfering in the sample volume a first scattering field that is generated by the interaction of the first portion of the first electromagnetic field and the first portion of the second electromagnetic field in the sample volume, with a second scattering field that is generated by the interaction of the second portion of the first electromagnetic field and the second portion of the second electromagnetic field in the local oscillator volume; and
    determining at least one of a real component and an imaginary component of the first scattering field responsive to interfering the first scattered field with the second scattered field.

12. The method as claimed in claim 11, wherein said method further includes the step of adjusting a phase difference between a first phase of the first scattering field and a second phase of the second scattering field.

13. The method as claimed in claim 11, wherein said method further includes the step of determining amplitude and phase information of the first scattering field responsive to an interference signal, and using said amplitude and phase information in the step of determining at least one of the real component and the imaginary component of the first scattering field is responsive to the amplitude and phase information.

14. The method as claimed in claim 11, wherein said method further includes the step of combining the second scattering field with the first and second electromagnetic fields in advance of the sample volume.

15. The method as claimed in claim 11, wherein said method further includes the steps of receiving an interference signal at a detector, and providing a detection signal to a phase locked amplifier.

16. A method of detecting a non-linear coherent field induced in a sample volume, said method comprising the steps of:

generating a first electromagnetic field at a first frequency;

generating a second electromagnetic field at a second frequency;

directing a first portion of said first electromagnetic field and a first portion of said second electromagnetic field through a first focusing lens toward the sample volume;

directing a second portion of said first electromagnetic field and a second portion of said second electromagnetic field through a second focusing lens toward a local oscillator volume;

combining a second scattering field that is generated by the interaction of the second portion of the first electromagnetic field and the second portion of the second electromagnetic field in the local oscillator volume, with the first and second electromagnetic fields in advance of the sample volume;

interfering a first scattering field that is generated by the interaction of the first portion of the first electromagnetic field and the first portion of the second electromagnetic field in the sample volume, with the second scattering field; and determining at least one of a real component and an imaginary component of the first scattering field responsive to interfering the first scattered field with the second scattered field.

17. The method as claimed in claim 16, wherein said method further includes the step of adjusting a phase difference between a first phase of the first scattering field and a second phase of the second scattering field.

18. The method as claimed in claim 16, wherein said method further includes the step of determining amplitude and phase information of the first scattering field responsive to an interference signal, and using said amplitude and phase information in the step of determining at least one of the real component and the imaginary component of the first scattering field is responsive to the amplitude and phase information.

19. The method as claimed in claim 16, wherein said method further includes the step of combining the first scattering field and the second scattering field in the sample volume.

20. The method as claimed in claim 16, wherein said method further includes the steps of receiving an interference signal at a detector, and providing a detection signal to a phase locked amplifier.

* * * * *

UNITED STATES PATENT AND TRADEMARK OFFICE
CERTIFICATE OF CORRECTION

| | | |
|---|---|---|
| PATENT NO. | : 7,388,668 B2 | Page 1 of 1 |
| APPLICATION NO. | : 11/145420 | |
| DATED | : June 17, 2008 | |
| INVENTOR(S) | : Eric O. Potma et al. | |

It is certified that error appears in the above-identified patent and that said Letters Patent is hereby corrected as shown below:

Please insert the following paragraph on Col. 1, line 5 of the issued patent:

GOVERNMENTAL SPONSORSHIP INFORMATION

This invention was made with U.S. government support under GM062536 awarded by the National Institutes of Health. The U.S. Government has certain rights in the invention.

Signed and Sealed this

Nineteenth Day of August, 2008

JON W. DUDAS
*Director of the United States Patent and Trademark Office*